US010626075B2

(12) United States Patent
Zhou et al.

(10) Patent No.: US 10,626,075 B2
(45) Date of Patent: Apr. 21, 2020

(54) PROCESS FOR OXIDATION OF ALCOHOLS USING OXYGEN-CONTAINING GASES

(71) Applicants: RHODIA OPERATIONS, Paris (FR); CENTRE NATIONAL DE LA RECHERCHE SCIENTIFIQUE, Paris (FR)

(72) Inventors: Wenjuan Zhou, Shanghai (CN); Wenhao Fang, Shanghai (CN); Armin T. Liebens, Shanghai (CN)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 16/207,635

(22) Filed: Dec. 3, 2018

(65) Prior Publication Data

US 2019/0100482 A1     Apr. 4, 2019

Related U.S. Application Data

(62) Division of application No. 15/574,524, filed as application No. PCT/CN2015/079188 on May 18, 2015, now Pat. No. 10,179,756.

(51) Int. Cl.
| | |
|---|---|
| *C07C 51/235* | (2006.01) |
| *B01J 37/03* | (2006.01) |
| *B01J 37/16* | (2006.01) |
| *B01J 23/89* | (2006.01) |
| *B01J 35/00* | (2006.01) |
| *C07C 231/12* | (2006.01) |
| *C07C 231/14* | (2006.01) |
| *C07C 51/23* | (2006.01) |
| *C07C 51/245* | (2006.01) |
| *B01J 21/04* | (2006.01) |
| *B01J 21/10* | (2006.01) |
| *B01J 23/06* | (2006.01) |
| *B01J 23/10* | (2006.01) |
| *C07C 59/125* | (2006.01) |
| *C07C 233/46* | (2006.01) |

(52) U.S. Cl.
CPC ............ *C07C 51/235* (2013.01); *B01J 21/04* (2013.01); *B01J 21/10* (2013.01); *B01J 23/06* (2013.01); *B01J 23/10* (2013.01); *B01J 23/894* (2013.01); *B01J 23/8926* (2013.01); *B01J 35/002* (2013.01); *B01J 35/006* (2013.01); *B01J 35/0013* (2013.01); *B01J 37/035* (2013.01); *B01J 37/16* (2013.01); *C07C 51/23* (2013.01); *C07C 51/245* (2013.01); *C07C 59/125* (2013.01); *C07C 231/12* (2013.01); *C07C 231/14* (2013.01); *C07C 233/46* (2013.01); *B01J 2231/70* (2013.01)

(58) Field of Classification Search
CPC ... C07C 231/12; C07C 233/46; C07C 51/235; C07C 59/125; C07C 231/14; C07C 51/23; C07C 51/245; B01J 21/04; B01J 21/10; B01J 2231/70; B01J 23/06; B01J 23/10; B01J 23/8926; B01J 23/894; B01J 35/0013; B01J 35/002; B01J 35/006; B01J 37/035; B01J 37/16
See application file for complete search history.

(56) References Cited

U.S. PATENT DOCUMENTS

| | | | |
|---|---|---|---|
| 3,342,858 A | 9/1967 | Fuhrmann et al. | |
| 4,214,101 A | 7/1980 | Miya et al. | |
| 5,292,940 A | 3/1994 | Noack et al. | |
| 5,463,114 A | 10/1995 | Noack et al. | |
| 8,093,414 B2 | 1/2012 | Klug et al. | |
| 2004/0199007 A1 | 10/2004 | Ostgard et al. | |
| 2010/0056735 A1 | 3/2010 | Stankowiak et al. | |
| 2010/0286418 A1* | 11/2010 | Klug ................... | C07C 231/14 554/63 |
| 2010/0305358 A1 | 12/2010 | Klug et al. | |
| 2011/0144385 A1 | 6/2011 | Franke et al. | |
| 2012/0296115 A1 | 11/2012 | Shirasawa et al. | |
| 2015/0210623 A1 | 7/2015 | Lemaire et al. | |

FOREIGN PATENT DOCUMENTS

| | | |
|---|---|---|
| CN | 101357333 A | 2/2009 |
| CN | 101905158 A | 12/2010 |
| DE | 3135946 A1 | 3/1983 |
| EP | 0300852 A1 | 1/1989 |
| EP | 0304763 A1 | 3/1989 |
| EP | 0388567 A1 | 9/1990 |
| JP | 5096516 | 7/1975 |
| JP | H04221339 A | 8/1992 |
| JP | 2011184379 A | 9/2011 |

(Continued)

OTHER PUBLICATIONS

Pina et al. (Highly selective oxidation of benzyl alcohol to benzaldehyde catalyzed by bimetallic gold-copper catalyst, Journal of Catalysis, 260, pp. 384-386, published 2008) (Year: 2008).*
Wang et al. (Selective oxidation of alcohols to aldehydes/ketones over copper oxide-supported gold catalysts, Journal of Catalysis, 299, pp. 10-19, published 2013) (Year: 2013).*
Heidkamp et al., "Oxidation of a tensidic alcohol to its corresponding carboxylic acid via Au catalysts", Eur. J. Lipid Sci. Technol. 2010, vol. 112, pp. 51-57.

(Continued)

*Primary Examiner* — Jafar F Parsa
*Assistant Examiner* — Blaine G Doletski

(57) ABSTRACT

The present invention concerns a process of oxidizing an alcohol for the production of its corresponding carbonyl compounds wherein the oxidation is performed with oxygen or gases containing oxygen in the presence of a catalyst comprising at least a gold compound and a copper compound. Said alcohol oxidation by gaseous oxidant can achieve a high yield and selectivity with minimized degradation products or waste organic solvents.

6 Claims, No Drawings

(56) References Cited

FOREIGN PATENT DOCUMENTS

| | | |
|---|---|---|
| JP | 2011184380 A | 9/2011 |
| JP | 2012149046 A | 8/2012 |
| JP | 2012149047 A | 8/2012 |
| JP | 29313067564 A | 4/2013 |
| JP | 2013151469 A | 8/2013 |
| WO | 2014020281 A1 | 2/2014 |
| WO | WO2016/026132 * | 9/2014 |

OTHER PUBLICATIONS

Heidkamp et al., "Catalyst development for the selective oxidation of ethoxylates to their corresponding ether carboxylic acids", Catalysis Communications, 2013, vol. 40, pp. 88-92.

Prüße et al., "Greener detergents—Gold-based catalysts for the production of ether carboxylic acids", events.dechema.de, Poster Program, Frankurt, In: 15th International Congress on Catalysis in Munich, Germany, Jul. 1-6, 2012.

Wang et. al., "Research Progress in Synthesis of Ethoxylated Fatty Alcohol Carboxylate by Catalytic Oxidation", Advances in Fine Petrochemicals, 2002, pp. 10-14. English language Abstract included.

Li et al., "Synthesis and Properties of Alcohol Ether Carboxylate", Speciality Petrochemicals, 2009, pp. 5-7. English language Abstract included.

Mehmet et al., "Catalytic Oxidation of fatty alcohol ethoxylates in a trickle-bed reactor", 4th Workshop on Fats and Oils as Renewable Feedstock for the Chemical Industry, Mar. 20-22, 2011, Karlsruhe, Germany, Program Lectures and Posters, p. 27, p. 82.

Heidkamp et al., Ceria supported gold-platinum catalysts for the selective oxidation of alkyl ethoxylates, Catalysis Science & Technology, 2013, vol. 3, pp. 2984-2992.

Brunauer et. al., "Adsorption of Gases in Multimolecular Layers", The Journal of American Society, 1938. vol. 60, p. 309-319.

Han et. al, Kinetics of ethylene combustion in the synthesis of vinyl acetate over a Pd/SiO2 catalyst, Journal of Catalysis, 2004, vol. 224, pp. 60-68.

* cited by examiner

PROCESS FOR OXIDATION OF ALCOHOLS USING OXYGEN-CONTAINING GASES

This application is a divisional of U.S. application Ser. No. 15/574,524, filed Nov. 16, 2017, which is a U.S. national phase entry under 35 U.S.C. § 371 of International Application No. PCT/CN2015/079188, filed on May 18, 2015. The entire contents of these applications are explicitly incorporated herein by this reference.

The present invention concerns a process of oxidizing an alcohol for the production of its corresponding carbonyl compounds wherein the oxidation is performed with oxygen or gases containing oxygen in the presence of a catalyst comprising at least a gold compound and a copper compound. Said alcohol oxidation by gaseous oxidant can achieve a high yield and selectivity with minimized degradation products or waste organic solvents.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Direct oxidation of fatty alcohols in the presence of noble metal catalyst(s) is known in the art and draws considerable interest, because this type of reaction has the potential to generate numerous fatty acid end-products with wide industrial uses, particularly in detergent and cosmetics applications.

For example, many publications described that ether carboxylic acids and/or their salts may be produced by oxidation of their corresponding ether alcohols, usually with the help of a noble metal catalyst. These publications include JP 50-96516 (KAO CORPORATION) Jul. 31, 1975, which discloses a process for preparing carboxylic acid salts by liquid phase dehydrogenative oxidation of ether alcohols in the presence of a palladium or platinum catalyst. Disadvantageously, this process needed a high reaction temperature of 100-270° C., which can easily degrade the ether link in the desired product.

To circumvent this high temperature problem, many later-published patents for this process chose to oxidize ether alcohols using oxygen or oxygen-containing gas in the presence of a noble metal catalyst, in most cases palladium or platinum, which generally allows a lower reaction temperature (e.g. 20-95° C.). See, for example, the description in U.S. Pat. No. 3,342,858 (ALLIED CHEMICAL CORPORATION) Sep. 19, 1967, U.S. Pat. No. 4,214,101 A (KAO SOAP CO., LTD) Jun. 22, 1980, DE 3135946 A (BAYER AG) Mar. 24, 1983, EP 0304763 A (HENKEL KGAA) Mar. 1, 1989, U.S. Pat. No. 5,292,940 A (HENKEL KGAA) Mar. 7, 1991, JP 2903187 B (KAWAKEN FINE CHEMICALS CO. LTD) Aug. 11, 1992, U.S. Pat. No. 5,463,114 A (HENKEL KGAA) Oct. 26, 1995, U.S. Pat. No. 8,093,414 B (CLARIANT INTERNATIONAL LTD) Feb. 21, 2008, US 2010056735 A (CLARIANT FINANCE BVI LTD) Oct. 23, 2008, US 20110144385 A (CLARIANT INTERNATIONAL LTD.) Feb. 11, 2010, CN 101357333 B (CHINA RESEARCH INSTITUTE OF DAILY CHEMICAL INDUSTRY) Feb. 4, 2009, US 20120296115 A (KAO CORP) Jul. 14, 2011, JP 2011184379 A (KAO CORP) Sep. 22, 2011, JP 2011184380 A (KAO CORP) Sep. 22, 2011, JP 2012149046 A (KAO CORP) Aug. 9, 2012, JP 2012149047 A (KAO CORP) Aug. 9, 2012, JP 2013067564 A (KAO CORP) Apr. 18, 2013 and JP 2013151469 A (KAO CORP) Jul. 4, 2013.

Nevertheless, while choosing oxygen-containing gases as oxidant is appealing for scaled up applications, these prior art oxidant processes do not satisfy all the efficiency, economic and environmental requirements for industrial use.

Thus, there is still a need in the art to provide an improved process for oxidizing alcohols, in particular fatty alcohols and the like, to obtain their corresponding carboxylic acid with a high yield and using an economically-viable catalyst solution.

INVENTION

The present invention relates to a process of oxidizing an alcohol of formula (I) for the production of its corresponding carbonyl compounds $$R\text{---}OH \qquad (I)$$

wherein R represents a saturated or unsaturated, linear, branched or cyclic $C_7$-$C_{50}$ hydrocarbon group which optionally comprises a heteroatom and which optionally comprises a substituent, wherein the oxidation is performed with oxygen or gases containing oxygen in the presence of a catalyst comprising at least a gold compound and a copper compound.

The invention also concerns a carbonyl compound susceptible to be obtained by the process as previously expressed.

As discovered by the present inventors, the alcohol oxidation by gaseous oxidant can achieve a high yield and selectivity by means of the above-described catalyst, with minimized degradation products or waste organic solvents. Moreover, the catalyst is also easy to recover and reuse, making it a cost and environmental viable option for industrial consideration.

It also appears that catalysts used in the process of the present invention showed the enhancement of the catalytic performance and provide a good catalyst stability and reusability in the repeated runs compared to monometallic catalyst.

Other characteristics, details and advantages of the invention will emerge even more fully upon reading the description which follows.

Definitions

Throughout the description, including the claims, the term "comprising one" should be understood as being synonymous with the term "comprising at least one", unless otherwise specified, and "between" should be understood as being inclusive of the limits.

Should the disclosure of any patents, patent applications, and publications which are incorporated herein by reference conflict with the description of the present application to the extent that it may render a term unclear, the present description shall take precedence.

As used herein, the term "hydrocarbon group" refers to a group consisting of carbon atoms and hydrogen atoms, which group may be saturated or unsaturated, linear, branched or cyclic, aliphatic or aromatic. Hydrocarbon groups of the present invention may be alkyl groups, alkenyl groups, alkynyl groups, aryl groups, alkylaryl groups, aryalkyl groups, heterocyclic groups, and/or alkylheterocyclic groups.

As used herein, the terminology "($C_n$-$C_m$)" in reference to an organic group, wherein n and m are each integers, indicates that the group may contain from n carbon atoms to m carbon atoms per group.

As used herein, "alkyl" groups include saturated hydrocarbons having one or more carbon atoms, including straight-chain alkyl groups, such as methyl, ethyl, propyl, butyl, pentyl, hexyl, heptyl, octyl, nonyl, decyl, cyclic alkyl groups (or "cycloalkyl" or "alicyclic" or "carbocyclic" groups), such as cyclopropyl, cyclopentyl, cyclohexyl, cycloheptyl, and cyclooctyl, branched-chain alkyl groups, such as isopropyl, tert-butyl, sec-butyl, and isobutyl, and alkyl-substituted alkyl groups, such as alkyl-substituted cycloalkyl groups and cycloalkyl-substituted alkyl groups. The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

As used herein, "alkenyl" or "alkenyl group" refers to an aliphatic hydrocarbon radical which can be straight or branched, containing at least one carbon-carbon double bond. Examples of alkenyl groups include, but are not limited to, ethenyl, propenyl, n-butenyl, i-butenyl, 3-methylbut-2-enyl, n-pentenyl, heptenyl, octenyl, decenyl, and the like. The term "alkynyl" refers to straight or branched chain hydrocarbon groups having at least one triple carbon to carbon bond, such as ethynyl.

The term "aryl group" includes unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle, such as tetralin. An "arylene" group is a divalent analog of an aryl group.

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups, such as pyrrolyl, pyridyl, isoquinolyl, quinolyl, purinyl, and furyl, may have aromatic character, in which case they may be referred to as "heteroaryl" or "heteroaromatic" groups.

Aryl and heterocyclic including heteroaryl groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfur, and phosphorus. Heterocyclic groups may be saturated or unsaturated or aromatic.

As used herein, the term "aralkyl" or "arylalkyl" means an alkyl group substituted with one or more aryl groups, such as, for example, phenylmethyl, phenylethyl, triphenylmethyl. The term "alkylaryl" means an alkyl moiety bound to an aryl moiety.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties.

The alcohol as used herein includes primary alcohols and secondary alcohols, preferably a primary alcohol.

The reaction encompassed in the process of oxidizing an alcohol for the production of its corresponding carbonyl compounds in the present invention notably includes a process of obtaining carboxylic acid from a primary alcohol, a process of obtaining aldehyde from a primary alcohol, and a process of obtaining ketone from a secondary alcohol.

As previously expressed, R represents a saturated or unsaturated, linear, branched or cyclic $C_7$-$C_{50}$ hydrocarbon group which optionally comprises a heteroatom and which optionally comprises a substituent. This group may then optionally comprise a heteroatom and/or a substituent. Preferably, R represents a saturated or unsaturated, linear, branched or cyclic $C_7$-$C_{50}$ hydrocarbon group which optionally comprises a heteroatom, such as for instance oxygen, nitrogen, sulfur, or halogen, and which optionally comprises a substituent.

A substituent may be for instance chosen in the group consisting of: an alkyl, an alkenyl, an aryl, an oxygen-containing group, such as hydroxyl, carbonyl, aldehyde, carboxyl, carboxylate, ester, alkoxy, hydroperoxy, ether, or acetal, and a nitrogen containing group, such as amine or amide. Substituent may preferably be selected from a group consisting of —$OR^3$, —$CH_3$, —$CH_2CH_3$, —COOH, —$CONH_2$ and —$COOR^3$, wherein $R^3$ represents an alkyl or aryl group.

The hydrocarbon group may be for instance substituted by 1, 2 or 3 identical or different substituent(s).

The alcohol subjected to oxidation according to the process of the present invention may be an ethoxylated alcohol of formula (II)

$$R^1(OCH_2CHR^2)_nOCH_2CH_2OH \qquad (II)$$

wherein: $R^1$ represents an alkyl radical having 1 to 22 carbon atoms or a monounsaturated or polyunsaturated linear or branched alkenyl radical having 1 to 22 carbon atoms, optionally comprising at least a substituent and/or a heteroatom such as N or O; $R^2$ represents a hydrogen atom or a methyl group or a mixture thereof in the individual molecule; and n has an average number between 2 and 20.

$R^1$ in formula (II) preferably represents an alkyl group having from 3 to 22, more preferably from 8 to 20 and most preferably from 10 to 16 carbon atoms. Particular preference for $R^1$ is given to methyl, butyl and lauryl, of which lauryl is further preferred. The $R^1$ group can be an alkyl group substituted with any substituent which does not interfere with the oxidation of the hydroxyl group. For example, $R^1$ in formula (II) may be an alkyl group substituted with at least one substituent selected from a group consisting of —$OR^3$, —$CH_3$, —$CH_2CH_3$, —COOH, —$CONH_2$ and —$COOR^3$, wherein $R^3$ represents an alkyl or aryl group.

In formula (II), the $R^2$ group on an individual molecule can be hydrogen, methyl or mixtures thereof. Accordingly, exemplary ethoxylated alcohol of formula (II) may be selected from a group consisting of straight ethoxylates, straight propoxylates and mixed ethoxylatepropoxylate, all being detergent range ethoxylate alcohols. Commercially, detergent range ethoxylate alcohols are available with an average of 3, 7, 9 and 12 ethoxylate units per molecule. Preparation of these detergent range ethoxylate alcohols are well known in the art.

Preferably, n is an integer of from 4 to 12, more preferably from 4 to 9 in the individual molecule of formula (II).

In particular, when the alcohol subjected to oxidation according to the process of the present invention is an ethoxylated alcohol of formula (II), the invention provides a process for producing compounds of formula (III)

$$R^1(OCH_2CHR^2)_nOCH_2COOB \quad (III)$$

with B being a cation and $R^1$, $R^2$ and n having the same meaning given above, and/or of the corresponding protonated carboxylic acids by oxidizing one or more ethoxylated alcohols of formula (II).

Preferably, the counterion B is an alkali metal cation preferably selected from a group consisting of Li, Na, K, Rb and Cs, of which Na and K are particularly preferred.

During the oxidation reaction in the basic medium, firstly the alkali metal salts of formula (III) are formed. To produce the free ether carboxylic acids (i.e. protonated carboxylic acids of compounds of formula (III)), the resulting alkali metal salts of formula (III) may be reacted with acids. Preferred acids are hydrochloric acid and sulphuric acid.

The alcohol subjected to oxidation according to the process of the present invention may also be a compound of formula (IV)

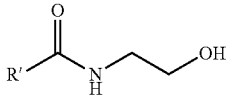

(IV)

wherein R' represents a saturated, linear or branched alkyl radical having from 4 to 25 carbon atoms or a monounsaturated or polyunsaturated linear or branched alkenyl radical having from 4 to 25 carbon atoms.

In the preferred compounds of formula (IV) according to the process of the present invention, R' is a saturated linear or branched alkyl radical having from 7 to 17 carbon atoms or a monounsaturated or polyunsaturated linear or branched alkenyl radical having from 7 to 17 carbon atoms, and is more preferably a saturated linear alkyl radical having from 9 to 14 carbon atoms.

As preferred examples of compounds of formula (IV), mentions can be made for a group consisting of lauric acid monoethanolamide, myristic acid monoethanolamide, caprylic acid monoethanolamide, capric acid monoethanolamide, palmitic acid monoethanolamide, stearic acid monoethanolamide and isostearic acid monoethanolamide, among which lauric acid monoethanolamide is particularly preferred. Here, it is also possible to use amides based on chain fractions or mixtures of these acid monoethanolamides, preferably coconut acid monoethanolamide.

In particular, when the alcohol subjected to oxidation according to the process of the present invention is a compound of formula (IV), the invention provides a process for producing compounds of formula (V)

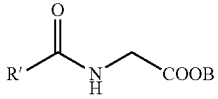

(V)

with B and R' having the same meaning given above, and/or of the corresponding protonated acylglycine acids by oxidizing one or more acid monoethanolamides of formula (IV).

During the oxidation reaction in the basic medium, firstly the alkali metal salts of formula (V) are formed. To produce the free ether acylglycine acids (i.e. protonated carboxylic acids of compounds of formula (V)), the resulting alkali metal salts of formula (V) may be reacted with acids. Preferred acids are hydrochloric acid and sulphuric acid.

Alternatively, in yet another embodiment, the alcohol subjected to oxidation according to the process of the present invention is selected from a group consisting of octanol, 1-decanol, 1-dodecanol, 1-tetradecanol, 1-hexadecanol, 1-octadecanol, 1-octadecenol, isoheptyl alcohol, cyclohexanol, cyclopentanol, cyclooctanol, (1r,3r,5r,7r)-adamantan-2-ol, thiophen-2-ylmethanol, 4-(hydroxymethyl) phenol, (E)-3-phenylprop-2-en-1-ol, bicyclo[2.2.1]heptan-2-ol, 2-hydroxy-5-butylbenzyl alcohol, isooctyl alcohol, isononyl alcohol, isodecyl alcohol, tridecyl alcohol and mixtures thereof.

The carbonyl compounds obtained by the reaction of the invention may notably be for instance a carboxylic acid or its salt, an aldehyde or a ketone. Preferably carboxylic acids are chosen in the group consisting of: polyoxyethylene (8-10) octyl ether carboxylic acid, polyoxyethylene (3-10) lauryl ether carboxylic acid, polyoxyethylene (3-10) polyoxyethylene(2-10) oleyl ether carboxylic acid, polyoxyethylene phenyl ether carboxylic acid, butylic acid, hexanoic acid, lauric acid, dodecanoic acid, docanoic acid, and hexadecanoic acid. Preferably aldehydes are chosen in the group consisting of: furan-2-carbaldehyde, thiophene-2-carbaldehyde, (2E,4E)-hexa-2,4-dienal, butyraldehyde, octanal, 4-hydroxybenzaldehyde, 2-hydroxy-5-methoxybenzaldehyde, and cinnamaldehyde. Preferably ketones are chosen in the group consisting of: cyclohexanone, cyclooctanone, cyclopentanone, acetophenone, hexan-2-one, (1r,3r,5r,7r)-adamantan-2-one, (E)-oct-3-en-2-one, 4-ethylcyclohexan-1-one, 3-methylcyclohexan-1-one, and 3,5-dimethylcyclohexan-1-one, bicyclo[2.2.1]heptan-2-one.

As previously expressed, catalyst of the present invention comprises at least a gold compound and a copper compound.

Gold compound of the present invention may be gold metal itself or any compound comprising gold such as for example salts or oxides of gold. Gold compounds are preferably chosen in the group consisting of: gold metal, gold oxide, gold nitrate, gold chloride, gold acetate, gold acetylacetonate, and gold hydroxide.

Preferably, the gold compound exists under the form of particles, and has an average particles size in the nanometer range, preferably from 1 to 50 nm and more preferably from 2 to 10 nm. The particle size can be measured, e.g., by transmission electron microscopy (TEM) or dynamic light scattering (DLS), powder X-ray diffraction (PXRD), $H_2$—$O_2$ titration, CO or $H_2$ chemo-adsorption methods known in the art.

Copper compound of the present invention may be copper metal itself or any compound comprising copper such as for example salts or oxides of copper. Copper compounds are preferably chosen in the group consisting of: copper metal, copper(I) oxide, copper(II) oxide, copper(III) oxide, copper nitrate, copper chloride, copper acetate, copper acetylacetonate, copper hydroxide, copper sulphate, and copper perchlorate.

Preferably, the copper compound exists under the form of particles, and has an average particles size in the nanometer range, preferably from 1 to 50 nm and more preferably from 2 to 10 nm. The particle size can be measured, e.g., by transmission electron microscopy (TEM) or dynamic light scattering (DLS) methods known in the art.

The molar ratio of the gold compound to the copper compound may be in the range of 2:1 to 100:1, preferably in the range of 3:1 to 61:1, more preferably in the range of 6:1 to 40:1.

Preferably, catalyst of the present invention is a heterogeneous catalyst.

Further preferably, the metal compounds are applied to a support. Preferred supports are activated carbon and oxide supports. Exemplary oxide supports include cerium dioxide, zinc oxide, titanium dioxide, magnesium oxide, iron oxide, lanthanum oxide, silica and aluminium oxide or their mixture, among which cerium dioxide and zinc oxide are particularly preferred.

Cerium oxide supports may have a specific surface comprised between 50 and 300 $m^2/g$, notably between 200 and 280 $m^2/g$, measured after calcination at a temperature of 350° C. for 2 hours. "Specific surface" notably means the specific B.E.T. surface determined by nitrogen adsorption in accordance with the ASTM D 3663-78 standard established by the BRUNAUER-EMMETT-TELLER method described in "The Journal of American Society, 60, 309 (1938)".

Cerium oxide supports may have a specific surface of at least 200 $m^2/g$, measured after calcination at a temperature of 400° C. for 2 hours. Cerium oxide supports may have a specific surface of at least 15 $m^2/g$, notably between 20 and 60 $m^2/g$, measured after calcination at a temperature of 800° C. for 2 hours.

Cerium oxide supports may have a porous volume of greater than 0.1 $cm^3/g$, preferably greater than 0.15 $cm^3/g$, notably between 0.15 and 0.25 $cm^3/g$, at a measurement temperature of 800° C. for 2 hours. The porous volume, which corresponds to pores with a diameter of less than 60 nm, is measured with a mercury porosimeter in accordance with the ASTM D4284-83 standard or using the isotherm nitrogen adsorption method (the above-identified B.E.T. method).

These cerium oxides are notably described in the EP300852 and EP388567 publications.

These cerium oxide supports may be obtained by calcination of a ceric hydroxide in which the cerium hydroxide is subjected to solvothermal treatment before calcination.

These cerium oxide supports may notably be obtained according to the following process consisting of:
preparing a ceric hydroxide by reacting a solution of cerium salt and a base, possibly in the presence of an oxidizing agent, with the amount of the base being such that the pH of the reaction medium is greater than 7; of separating the precipitate obtained, and possibly washing it;
placing the ceric hydroxide in suspension in water or in an aqueous solution of a decomposable base;
heating it in a closed chamber to a temperature and a pressure respectively lower than the critical temperature and the critical pressure of said medium;
cooling the reaction mixture and bringing it to atmospheric pressure;
separating the ceric hydroxide treated in this manner; then calcining it.

Cerium oxide particles may also comprise at least one rare earth element oxide, other than cerium oxide, an alkaline earth metal oxide, a transition metal element oxide, a post-transition metal element oxide, or a metalloid element oxide, notably in a proportion comprised between 1 and 40% by weight of oxide, preferably in a proportion comprised between 1 and 20% by weight of oxide.

Rare earth element (REE) or rare earth metal is one of a set of seventeen chemical elements in the periodic table, meaning the fifteen lanthanides plus scandium and yttrium. Preferably, the rare earth element oxides are chosen in the group consisting of: lanthanium oxide ($La_2O_3$), praseodymium oxide ($Pr_6O_{11}$), neodymium oxide ($Nd_2O_3$) and yttrium oxide ($Y_2O_3$).

Transition metal element oxide may be for instance $ZrO_2$ and $TiO_2$. Post-transition metal element oxide may be for instance $Al_2O_3$, $CuO$ and $ZnO$. Metalloid element oxide may be for instance $SiO_2$. Alkaline earth metal oxide may be for instance $BaO$.

Preferred mixed oxides of the present invention are chosen in the group consisting of: $CeO_2$—$ZrO_2$, $CeO_2$—$SiO_2$, $CeO_2$—$Pr_2O_3$, and $CeO_2$—$ZrO_2$—$La_2O_3$.

Catalysts composed of a cerium oxide support and comprising at least a gold compound and a copper compound may be obtained by several know methods such as for example adsorption, deposition-precipitation, impregnation or co-precipitation, notably incipient wetness impregnation. Several gold and coppers compounds or gold and copper compound precursors may be used.

Impregnation of an appropriate catalyst support is notably mentioned in Y.-F. Han et al. Journal of Catalysis 224 (2004) 60.

The activation or re-activation of the catalysts may involve a calcination step and/or a reduction step under hydrogen. Notably, the activation of the modified catalysts may involve a calcination step under air or $O_2$ at 100-500° C. for 1-24 hours and a reduction step under hydrogen at the same temperature for 1-6 hours. It is also possible to activate the catalyst of the present invention by reduction in a flow of hydrogen at 100-500° C. It is also possible to activate or re-activate the catalyst of the present invention by in situ reduction with sodium borohydride, sodium ascorbate, citric acid, or hydrazine.

The concentration of gold compound on cerium oxide may be comprised between 0.1 and 10% by weight, preferably from 0.5 to 4% by weight.

The concentration of copper compound on cerium oxide may be comprised between 0.005 and 6% by weight, preferably from 0.01 to 3% by weight.

The weight ratio of the catalyst of the present invention to the alcohol may be comprised between 0.04 and 0.20, preferably comprised between 0.06 and 0.13.

The oxidation reaction according to the process of the invention is usually carried out at a temperature between 30° C. and 100° C., preferably between 40° C. and 90° C.

The reaction pressure is generally higher than atmospheric pressure, although higher pressure is also possible, notably comprised between 3 and 20 bar.

The reaction time is generally between 1 hour and 30 hours, preferably between 3 hours and 20 hours.

The process of the invention is preferably carried out in an aqueous medium. For the purpose of the present invention, the term "aqueous medium" refers to a medium which contains liquid water, for at least 50 molar percent and preferably at least 80 molar percent of the totality of the medium. Specifically, the aqueous medium according to the present invention may be a homogeneous or heterogeneous medium, such as a biphasic or multiphasic system comprising an aqueous phase.

Further preferably, the process of the invention is carried out in an aqueous medium containing a base compound. Said base compound may be selected from carbonates, hydroxides and oxides, and is preferably selected from hydroxides of formula BOH with B as defined above.

The pH during the oxidation reaction is preferably between 9 and 15, more preferably between 10 and 14.

Optionally, a uniform pH value is maintained throughout the oxidation reaction by adding a base compound in a given range.

According to the present invention, the oxidation is performed with oxygen or gases containing oxygen, such as notably air, $O_2$—$N_2$, and $O_2$—Ar.

At the end of the reaction, the carbonyl compounds may be isolated by known methods, such as neutralization and solvent extraction.

The present invention also concerns a composition comprising at least an alcohol of formula (I)

$$R—OH \qquad (I)$$

wherein R represents a saturated or unsaturated, linear, branched or cyclic $C_7$-$C_{50}$ hydrocarbon group which optionally comprises a heteroatom and which optionally comprises a substituent, and a catalyst comprising at least a gold compound and a copper compound.

The following examples are provided to illustrate preferred embodiments of the invention and are not intended to restrict the scope thereof. Other aspects, advantages and modifications within the scope of the invention will be apparent to those skilled in the art to which the invention pertains.

Experimental Part

Preparation of Catalysts

Gold and copper nanoparticles were adsorbed on cerium oxide using the following procedure: 350 mL aqueous solution of gold (III) chloride trihydrate (0.082 g, $HAuCl_4.3H_2O$, Mw=393.83, Au 49.0%) and certain amount of copper (II) chloride dihydrate (the Au:Cu molar ratio of 1:0.1 or 1:0.5, respectively. $CuCl_2.2H_2O$, Mw=170.48, $CuCl_2.2H_2O$ 99%) in deionized water was added to 20 mL aqueous solution of 2.0 g cerium oxide ($CeO_2$, Actalys HSA20SP from Solvay) in deionized water. The resulting slurry was continuously stirred for 1 hour at room temperature. To this, 5 mL aqueous solution of sodium borohydride (0.13 g, Mw=37.83, $NaBH_4$ 98%) in deionized water was dropwise added. The Au—Cu/$CeO_2$ solid thus produced was filtered and washed with several litres of deionized water until no trace of chloride was detected by the $AgNO_3$ test, and then freeze-dried under vacuum for 24 hours. The dried Au—Cu/$CeO_2$ solid was analysed by chemical analysis and transition electronic microscopy (TEM), to determine the content and size of gold and copper nanoparticles on the $CeO_2$ support. The real contents of gold and copper on commercial $CeO_2$ were 1.1 wt % Au, 0.11 wt % Cu and 1.0 wt % Au, 0.063 wt % Cu, respectively.

The 1% Au/$CeO_2$ catalyst was prepared according to the above method except the addition of Cu source.

Catalysts Test: Oxidizing Ethoxylated Alcohol Using Various Catalysts

The catalysts obtained from previous examples were used for oxidizing ethoxylated alcohol, which was carried out in a high-pressure batch reactor. Specifically, 49.2 mg of 1 wt % Au/$CeO_2$ catalyst was added into 2.6 g aqueous solution of 24 wt % polyoxyethylene lauryl ether (AEO 7 obtained from Sasol, with a Mw of 494.7) containing 55.1 mg (1.9 mmol) of NaOH, giving a NaOH/alcohol molar ratio of 1.1 and an alcohol/metal molar ratio of 500 in the mixture. The reactor was pressurized with oxygen to a pressure of 12 bar and then sealed. The mixture was heated to the reaction temperature of 80° C. under a gentle stirring (600-800 rpm) for 4 h. The end products in the reactor were analyzed and quantified by 1H NMR and 13C NMR, which found that polyoxyethylene lauryl ether was converted sodium polyoxyethylene lauryl ether carboxylate, according to the data as provided in Table 1:

TABLE 1

| Example | Catalyst | Product yield % | T.O.N |
|---|---|---|---|
| 1 | 1.1 wt % Au-0.11 wt % Cu/$CeO_2$ ratio:alcohol:Au + Cu = 250:1 reaction time: 16 h pressure: 17 bar | 85.1 | 213 |
| 2 | 1.0 wt % Au-0.063 wt % Cu/$CeO_2$ ratio:alcohol:Au + Cu = 500:1 reaction time: 4 h pressure: 12 bar | 81.4 | 407 |
| C1 | 1 wt % Au/$CeO_2$ ratio:alcohol:Au = 500:1 reaction time: 4 h pressure: 12 bar | 73.0 | 365 |
| C2 | $CeO_2$ Actalys HSA20SP reaction time: 4 h pressure: 12 bar | 0 | 0 |

T.O.N means the molar ratio of product per gold.

It appears then that the activity of bimetallic Au/Cu catalyst exceeds the activity of the monometallic Au catalyst. Furthermore, it appears that the bimetallic Au/Cu catalyst stability and reusability in the repeated runs is higher with a maintained high product yield, compared to monometallic Au catalyst.

The invention claimed is:

1. A composition comprising an ethoxylated alcohol of formula (II)

$$R^1(OCH_2CHR^2)_nOCH_2CH_2OH \qquad (II)$$

wherein $R^1$ represents an alkyl radical having 1 to 22 carbon atoms or a monounsaturated or polyunsaturated linear or branched alkenyl radical having 2 to 22 carbon atoms, optionally comprising at least a substituent and/or a heteroatom; $R^2$ represents a hydrogen atom or a methyl group or a mixture thereof in the individual molecule; and n has an average number between 2 and 20;

or an acid monoethanolamide of formula (IV)

(IV)

wherein R' represents a saturated, linear or branched alkyl radical having from 4 to 25 carbon atoms or a monounsaturated or polyunsaturated linear or branched alkenyl radical having from 4 to 25 carbon atoms;

and a catalyst comprising at least a gold compound and a copper compound.

2. The composition of claim 1, wherein $R^1$ is selected from a group consisting of methyl, butyl and lauryl.

3. The composition of claim 1, wherein $R^1$ is an alkyl group substituted with at least one substituent selected from a group consisting of —$OR^3$, —$CH_3$, —$CH_2CH_3$, —COOH, —$CONH_2$ and —$COOR^3$, wherein $R^3$ represents an alkyl or aryl group.

4. The composition according to claim 1, wherein the acid monoethanolamide of formula (IV) is lauric acid monoethanolamide.

5. The composition according to claim 1, wherein the catalyst is applied to a support selected from the group consisting of activated carbon and oxide supports.

6. The composition according to claim 5, wherein the support is an oxide support selected from the group consisting of zinc oxide, magnesium oxide, cerium dioxide and aluminium oxide.

* * * * *